(12) United States Patent
Moctezuma De La Barrera et al.

(10) Patent No.: US 7,166,114 B2
(45) Date of Patent: Jan. 23, 2007

(54) METHOD AND SYSTEM FOR CALIBRATING A SURGICAL TOOL AND ADAPTER THEREOF

(75) Inventors: Jose Luis Moctezuma De La Barrera, Freiburg (DE); Amir Sarvestini, Freiburg (DE)

(73) Assignee: Stryker Leibinger GmbH & Co KG, Freiburg (DE)

( * ) Notice: Subject to any disclaimer, the term of this patent is extended or adjusted under 35 U.S.C. 154(b) by 231 days.

(21) Appl. No.: 10/246,599

(22) Filed: Sep. 18, 2002

(65) Prior Publication Data

US 2004/0054489 A1 Mar. 18, 2004

(51) Int. Cl.
*A61B 19/00* (2006.01)
*A61B 19/12* (2006.01)

(52) U.S. Cl. .......................... 606/130; 606/1
(58) Field of Classification Search ................ 600/414, 600/424, 426–7, 427, 429; 606/1, 130
See application file for complete search history.

(56) References Cited

U.S. PATENT DOCUMENTS

| 4,383,373 A | 5/1983 | Couturier ..................... 33/286 |
| 4,567,896 A | 2/1986 | Barnea et al. ............... 128/660 |
| 4,722,056 A | 1/1988 | Roberts et al. ............. 364/413 |
| 5,050,608 A | 9/1991 | Watanabe et al. ....... 128/653 R |

(Continued)

FOREIGN PATENT DOCUMENTS

CA 1336451 7/1995

(Continued)

OTHER PUBLICATIONS

Peshkin et al., "Diagramming Registration Connectivity and Structure", Medicine Meets Virtual Reality III, pp. 1-10 (Jan. 1995).

(Continued)

*Primary Examiner*—Linda C. M. Dvorak
*Assistant Examiner*—Aaron Roane
(74) *Attorney, Agent, or Firm*—McCracken & Frank LLP

(57) ABSTRACT

A method for easily calibrating both the position of the tip of a surgical tool and the orientation of that tool includes attaching a tracking device capable of communication with the surgical navigation system to the surgical tool using an adapter, where the adapter has a known relation between the tracking device and the axis of the surgical tool. The method then performs a calibration process to calculate the position of the tip of the surgical tool and the position of the tracking device and orientation data for the surgical tool from the known relation between the tracking device and the axis of the surgical tool and from the tool tip position. Lastly, the method stores the position of the tool tip for the surgical tool and the orientation data within memory of the surgical navigation system so the position and the orientation of the surgical tool can be tracked by the surgical navigation system.

The adapter has a body with an interior surface that defines an opening through which a surgical tool can be inserted, the opening having an axis. The adapter also has a docking structure for a tracking device such that there is a known relation between the tracking device and the axis of the opening and the axis of a tool that is inserted in the opening.

20 Claims, 16 Drawing Sheets

U.S. PATENT DOCUMENTS

| | | | |
|---|---|---|---|
| 5,056,523 A | 10/1991 | Hotchkiss, Jr. et al. | 128/653 R |
| 5,078,140 A | 1/1992 | Kwoh | 128/653.1 |
| 5,142,930 A | 9/1992 | Allen et al. | 74/469 |
| 5,186,174 A | 2/1993 | Schlondorff et al. | 128/653.1 |
| 5,197,476 A | 3/1993 | Nowacki et al. | 128/660.03 |
| 5,198,877 A | 3/1993 | Schulz | 356/375 |
| 5,222,499 A | 6/1993 | Allen et al. | 128/653.1 |
| 5,230,623 A | 7/1993 | Guthrie et al. | 433/72 |
| 5,251,127 A | 10/1993 | Raab | 364/413.13 |
| 5,299,288 A | 3/1994 | Glassman et al. | 395/80 |
| 5,305,203 A | 4/1994 | Raab | 364/413.13 |
| 5,309,913 A | 5/1994 | Kormos et al. | 128/653.1 |
| 5,383,454 A | 1/1995 | Bucholz | 128/653.1 |
| 5,389,101 A | 2/1995 | Heilbrun et al. | 606/130 |
| 5,392,384 A | 2/1995 | Tounai et al. | 395/89 |
| 5,394,875 A | 3/1995 | Lewis et al. | 128/660.09 |
| 5,471,312 A | 11/1995 | Watanabe et al. | 358/296 |
| 5,483,961 A | 1/1996 | Kelly et al. | 128/653.1 |
| 5,494,034 A | 2/1996 | Schlondorff et al. | 128/653.1 |
| 5,517,990 A | 5/1996 | Kalfas et al. | 128/653.1 |
| 5,564,437 A | 10/1996 | Bainville et al. | 128/774 |
| 5,617,857 A | 4/1997 | Chader et al. | 128/653.1 |
| 5,622,170 A | 4/1997 | Schulz | 128/653.1 |
| 5,662,111 A | 9/1997 | Cosman | 128/653.1 |
| 5,663,795 A | 9/1997 | Rueb | 356/375 |
| 5,676,673 A | 10/1997 | Ferre et al. | 606/130 |
| 5,732,703 A | 3/1998 | Kalfas et al. | 128/653.1 |
| 5,740,222 A | 4/1998 | Fujita et al. | 378/4 |
| 5,748,696 A | 5/1998 | Fujita et al. | 378/4 |
| 5,772,594 A | 6/1998 | Barrick | 600/407 |
| 5,787,886 A | 8/1998 | Kelly et al. | 128/653.1 |
| 5,848,126 A | 12/1998 | Fujita et al. | 378/195 |
| 5,848,967 A | 12/1998 | Cosman | 600/426 |
| 5,851,183 A | 12/1998 | Bucholz | 600/425 |
| 5,876,325 A | 3/1999 | Mizuno et al. | 600/102 |
| 5,891,034 A | 4/1999 | Bucholz | 600/426 |
| 5,921,992 A | 7/1999 | Costales et al. | 606/130 |
| 5,967,982 A | 10/1999 | Barnett | 600/429 |
| 5,987,960 A | 11/1999 | Messner et al. | 73/1.79 |
| 5,999,837 A | 12/1999 | Messner et al. | 600/407 |
| 6,006,126 A | 12/1999 | Cosman | 600/426 |
| 6,021,343 A | 2/2000 | Foley et al. | 600/429 |
| 6,112,113 A | 8/2000 | Van Der Brug et al. | 600/427 |
| 6,167,295 A | 12/2000 | Cosman | 600/426 |
| 6,266,551 B1 | 7/2001 | Osadchy et al. | 600/424 |
| 6,273,896 B1 * | 8/2001 | Franck et al. | 606/130 |
| 6,275,725 B1 | 8/2001 | Cosman | 600/426 |
| 6,282,437 B1 | 8/2001 | Franck et al. | 600/429 |
| 6,285,902 B1 | 9/2001 | Kienzle, III et al. | 600/427 |
| 6,298,262 B1 | 10/2001 | Franck et al. | 600/426 |
| 6,306,126 B1 | 10/2001 | Moctezuma | 606/1 |
| 6,335,617 B1 | 1/2002 | Osadchy et al. | 324/202 |
| 6,370,411 B1 | 4/2002 | Osadchy et al. | 600/372 |
| 6,428,547 B1 | 8/2002 | Vilsmeier et al. | 606/130 |
| 6,442,416 B1 | 8/2002 | Schultz | 600/429 |
| 2001/0027271 A1 | 10/2001 | Franck et al. | 600/426 |
| 2001/0034530 A1 | 10/2001 | Malackowski et al. | 606/130 |
| 2002/0016599 A1 | 2/2002 | Kenzle, III. | 606/130 |
| 2002/0077540 A1 | 6/2002 | Kienzle, III. | 600/424 |
| 2002/0077543 A1 | 6/2002 | Grzeszczuk et al. | 600/424 |
| 2002/0077544 A1 | 6/2002 | Shahidi | 600/424 |

FOREIGN PATENT DOCUMENTS

| | | |
|---|---|---|
| EP | 326 768 A2 | 12/1988 |
| EP | 469 966 A1 | 7/1991 |
| JP | 55-73253 | 6/1980 |
| JP | 57-21250 | 2/1982 |
| JP | 61-25531 | 2/1986 |
| JP | 61-31129 | 2/1986 |
| JP | 1-245108 | 9/1989 |
| JP | 03-057466 | 3/1991 |
| JP | 05-049644 | 3/1993 |
| JP | 405111886 A | 5/1993 |
| JP | 07-194616 | 8/1995 |
| JP | 07-236633 | 9/1995 |
| JP | 07-323035 | 12/1995 |
| JP | 07-328016 | 12/1995 |
| JP | 08-010266 | 1/1996 |
| JP | 08-38507 | 2/1996 |
| WO | WO 91/04711 | 4/1991 |
| WO | WO 91/07726 | 5/1991 |
| WO | WO 92/06645 | 4/1992 |
| WO | WO 94/23647 | 10/1994 |
| WO | WO 94/24933 | 11/1994 |
| WO | WO 96/11624 | 4/1996 |
| WO | WO 96/32059 | 10/1996 |
| WO | WO 97/15234 | 5/1997 |
| WO | WO 97/29678 | 8/1997 |

OTHER PUBLICATIONS

Ahlers et al., "Calibration Requirements and Procedures for a Monitor-Based Augmented Reality System", European Computer Industry Research Centre, pp. 1-32 (Jul. 6, 1995).

Viergever et al. "An Overview of Medical Image Registration Methods", Imaging Science Department, Imaging Center Utrecht, pp. 1-22.

Stulberg et al., "A Computer-Assisted Total Knee Replacement Surgical System Using a Calibrated Robot", Northwestern University, pp. 1-28.

Peshkin et al, "Complete Parameter Identification of a Robot From Partial Pose Information" Northwestern University, pp. 1-26.

Rose et al, "Object Calibration for Augmented Reality", European Computer-Industry Research Centre GmbH, pp. I-III, 1-18 (Aug. 1995).

Bergmann et al., "Calibration of Tracking Systems in a Surgical Environment", IEEE Transactions on Medical Imaging, pp. 1-6 (Oct. 1988).

Jiang et al., "Interactive Intraoperative Localization Using an Infrared-Based System", Wayne State University, pp. 84-88 (Oct. 1993).

Reinhardt et al., "Micro-Stereometry: A Frameless Computerized Navigating System For Open Microsurgery", Computerized Medical Imaging and Graphics vol. 18, pp. 229-233 (1994).

Long et al., "An Optical 3D Digitizer for Frameless Stereotactic Surgery", IEEE Computer Graphics and Applications pp. 55-64 (1996).

Kadi et al., "Computer-Assisted Neurosergery System: Wayne State University Hardware and Software Configuration", Computerized Medical Imaging and Graphics, vol. 18, No. 4, pp. 257-271 (1994).

Bucholz et al., "Frameless Stereotactic Ultrasonograph Computerized Medical: Method and Applications", Imaging and Graphics, vol. 18, No. 4, pp. 235-246 (1994).

Phillips et al., "Image Guided Orthopaedic Surgery Design and Analysis", Transactions of the Institute of Measurement and Control vol. 17, No. 5, pp. 251-264 (1995).

* cited by examiner

METHOD AND SYSTEM FOR CALIBRATING A SURGICAL TOOL AND ADAPTER THEREOF

FIELD OF THE INVENTION

This invention generally relates to calibrating surgical tools for use with a surgical navigation system. More particularly this invention relates to the calibration of a combination of a universal tracking device and the surgical tool so that the position and orientation of the surgical tool can be determined by the surgical navigation system.

BACKGROUND OF THE INVENTION

The use of image guided surgical navigation systems for assisting surgeons in performing delicate surgery has become more common. Typical surgical navigation systems utilize specially developed tools that include built in tracking devices so that the surgeon can see the position of the surgical tool overlaid on a monitor that shows a preoperative image or an intraoperative image. The preoperative images are typically prepared using well-known preoperative scanning techniques, such as MRI or CT scans. The intraoperative images can be prepared using flouroscope, low level x-ray and similar devices. The tracking devices typically include multiple optical emitters, such as LED's, that can be detected by the surgical navigation system. From the position of the emitters, the surgical navigation system can determine the position and/or orientation of the surgical tool.

As used in this specification, the term position means the coordinates of the tip of the surgical tool in three-dimensional space, the x, y, z or Cartesian coordinates, relative to the surgical navigation system. The term orientation means the pitch, roll, and yaw of the surgical tool. When both the position and the orientation of a surgical tool are defined, the absolute position of that surgical tool is known to the surgical navigation system.

In order for a surgeon to use a surgical tool without a built in tracking device with a surgical navigation system, a universal tracking device must be attached to the surgical tool. The universal tracking device and the surgical tool combination must be calibrated so that the surgical navigation system knows the relation between tip of the surgical tool and the position of the tracking device. Surgical tools with the attached universal tracking device can be calibrated and then tracked. If the tracking device and surgical tool have been calibrated relative to the surgical navigation system so that only the position of the tip of the surgical tool is known to the surgical navigation system, then only the position of the tip but not the orientation of the surgical tool can be tracked by the system. Because the exact path the surgeon will take during a particular surgical procedure is very important, it is preferable to know both the position and orientation of the surgical tools used during that procedure so that the surgical tools can be completely represented on the monitor of typical surgical navigation systems.

In order to provide both position and orientation data for the combination of the surgical tool and the attached universal tracking device, both the position and orientation for each surgical tool and tracking device combination must be calibrated. Typical prior calibration devices have been described in U.S. Pat. Nos. 5,987,960, 5,921,992 and 6,306, 126. Each of these calibration devices utilizes the principal of constraining the axis of the surgical tool in a plane perpendicular to a base of the calibration device. Because the position of the base of the calibration device and the position of the axis of the surgical tool are known relative to optical tracking elements contained on the calibration device, the surgical navigation system can calculate the position and the orientation for the particular surgical tool and the tracking device combination. Thereafter, that surgical tool and tracking device combination can be completely tracked by the surgical navigation system.

SUMMARY OF THE INVENTION

The present invention is directed to an improved method of calibrating both the position and orientation of a surgical tool for use with a surgical navigation system. This method includes the steps of attaching a tracking device capable of communicating with the surgical navigation system to the surgical tool using an adapter, wherein the surgical tool has both a tool axis and a tool tip and the adapter has a known relation between the tracking device and the tool axis. The method further includes the step of touching the tool tip to a calibration device capable of communicating with the surgical navigation system and capable of determining the position of the tool tip relative to the position of the tracking device. The method further includes the step of calculating the position of the tool tip and then calculating orientation data for the surgical tool from the known relation between the tracking device and the tool axis. Lastly, the method includes the step of storing the position of the tool tip and the orientation data for the surgical tool within memory of the surgical navigation system so that when the surgical tool is used with the surgical navigation system, the position and the orientation of the surgical tool can be tracked by the surgical navigation system.

A further method of the present invention for calibrating the position and the orientation of the surgical tool for use with the surgical navigation system comprises the following steps. The first step is attaching a tracking device capable of communicating with the surgical navigation system to the surgical tool using an adapter wherein the surgical tool has a tool axis and a tool tip and the adapter has a known relation between the tracking device and the tool axis. The second step in the method is touching the tool tip to a calibration device capable of communicating with the surgical navigation system and capable of determining a position of the tip of the surgical tool relative to a position of the tracking device. The method further includes the step of calculating the position of tool tip and the step of storing the position of the tool tip within memory of the surgical navigation system. Lastly, the method includes the step of determining orientation data for the surgical tool from the position of the tool tip and from a database of stored relations of the tracking device to the tool axis and from the position of the tool tip such that the position of the tool tip intersects an axis of the surgical tool from the database so that when the surgical tool is used with the surgical navigation system, the position and orientation of the surgical tool can be tracked by the surgical navigation system.

The present invention also is directed to an adapter to attach a tracking device to a surgical tool having axis, which comprises a body having an exterior surface, and an interior surface. The adapter also includes a docking structure for the tracking device attached to the exterior surface. Lastly, the adapter includes the interior surface that defines an opening extending through the body, the opening having an axis and the opening having a shape to engage the surgical tool such that there is identity between the axis of the opening and the tool axis.

The present invention further includes a system for the calibration of a surgical tool for use with a surgical navigation system. The system comprises a memory unit, an adapter that can be attached to a surgical tool having a tool tip and a tool axis, and a tracking device attached to the adapter, the tracking device capable of being tracked by the surgical navigation system, wherein the adapter has a known relation between the tracking device and the tool axis. The system further includes a calibration device capable of determining the position of the tool tip relative to the position of the tracking device and capable of communicating with the surgical navigation system. The system also includes a first circuit operative to calculate the position of the tool tip relative to a position of the tracking device and an orientation of the surgical tool from the known relation between the tracking device and the tool axis and from the position of the tool tip, and a second circuit operative to store the position of the tool tip and the orientation of the tool in the memory unit.

A further system of the present invention for calibrating a position and an orientation of a surgical tool for use with a surgical navigation system comprises means for attaching a tracking device capable of communication with the surgical navigation system to the surgical tool using an adapter, the surgical tool having a tool axis and a tool tip, and the adapter having a known relation between the tracking device and the tool axis. The system also includes means for calculating a position of the tool tip by touching the tool tip to a calibration device capable of communication with the surgical navigation system and capable of determining the position of the tool tip relative to a position of the tracking device and means for calculating orientation data for the surgical tool from the known relation between the tracking device and the tool axis and from the position of the tool tip. In addition, the system includes means for storing the position of the tool tip for the surgical tool and the orientation data for the surgical tool within memory of the surgical navigation system so that when the surgical tool is used with the surgical navigation system, the position and the orientation of the surgical tool can be tracked by the surgical navigation system.

A still further system of the present invention for calibrating a surgical tool for use with a surgical navigation system comprises a memory unit and means for attaching an adapter to a surgical tool having a tool tip and a tool axis. The system also includes means for tracking the surgical tool attached to the adapter, the tracking means capable of being tracked by the surgical navigation system, wherein the adapter has a known relation between the tracking device and the tool axis and means for calibrating capable of determining a position of the tool tip relative to the position of the tracking means and capable of communicating with the surgical navigation system. The system further includes means for calculating the position of the tool tip; and an orientation of the surgical tool from the known relation between the tracking device and the tool axis and from the position of the tool tip, and means for storing the position of the tool tip and the orientation of the surgical tool in the memory unit.

Another system of the present invention for calibrating a position and an orientation of a surgical tool for use with a surgical navigation system comprises means for attaching a tracking device capable of communication with the surgical navigation system to the surgical tool using an adapter, the surgical tool having a tool axis and a tool tip, and the adapter having a known relation between the tracking device and the tool axis. The system also includes means for calculating a position of the tool tip by touching the tool tip to a calibration device capable of communicating with the surgical navigation system and capable of determining the position of the tool tip relative to a position of the tracking device, and means for storing the position of tool tip within memory of the surgical navigation system. In addition the system has means for determining orientation data for the surgical tool from the position of the tool tip and from a database of stored relations of the tracking device to the tool axis and from the position of the tool tip, such that the position of the tool tip intersects an axis of the surgical tool from the database, so that when the surgical tool is used with the surgical navigation system the position and the orientation of the surgical tool can be tracked by the surgical navigation system.

Other aspects and advantages of the present invention will become apparent upon consideration of the following detailed description.

DESCRIPTION OF THE PREFERRED EMBODIMENTS

Figure 1:
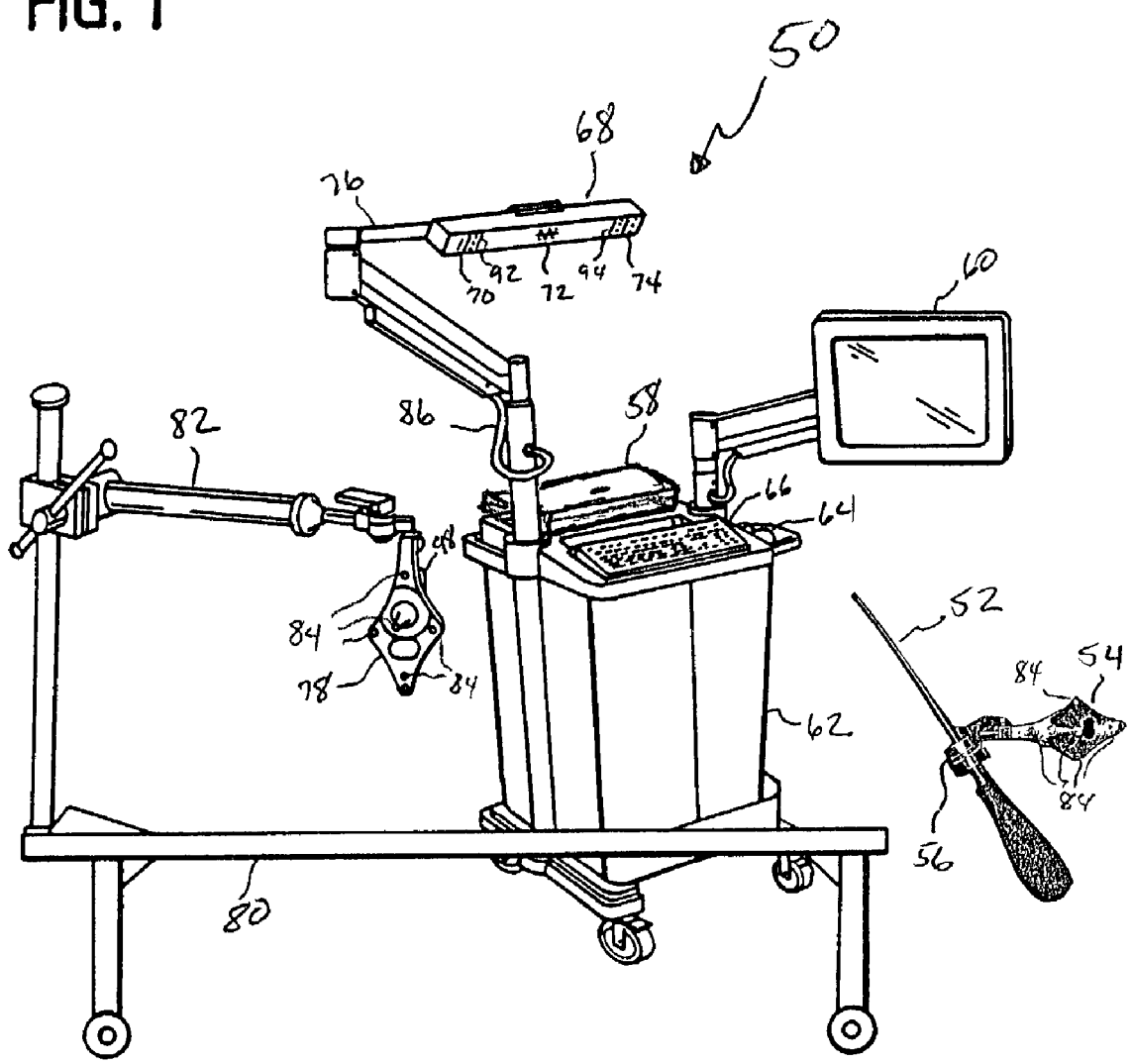
FIG. 1 is a schematic view of the surgical navigation system.
Figure 1A:
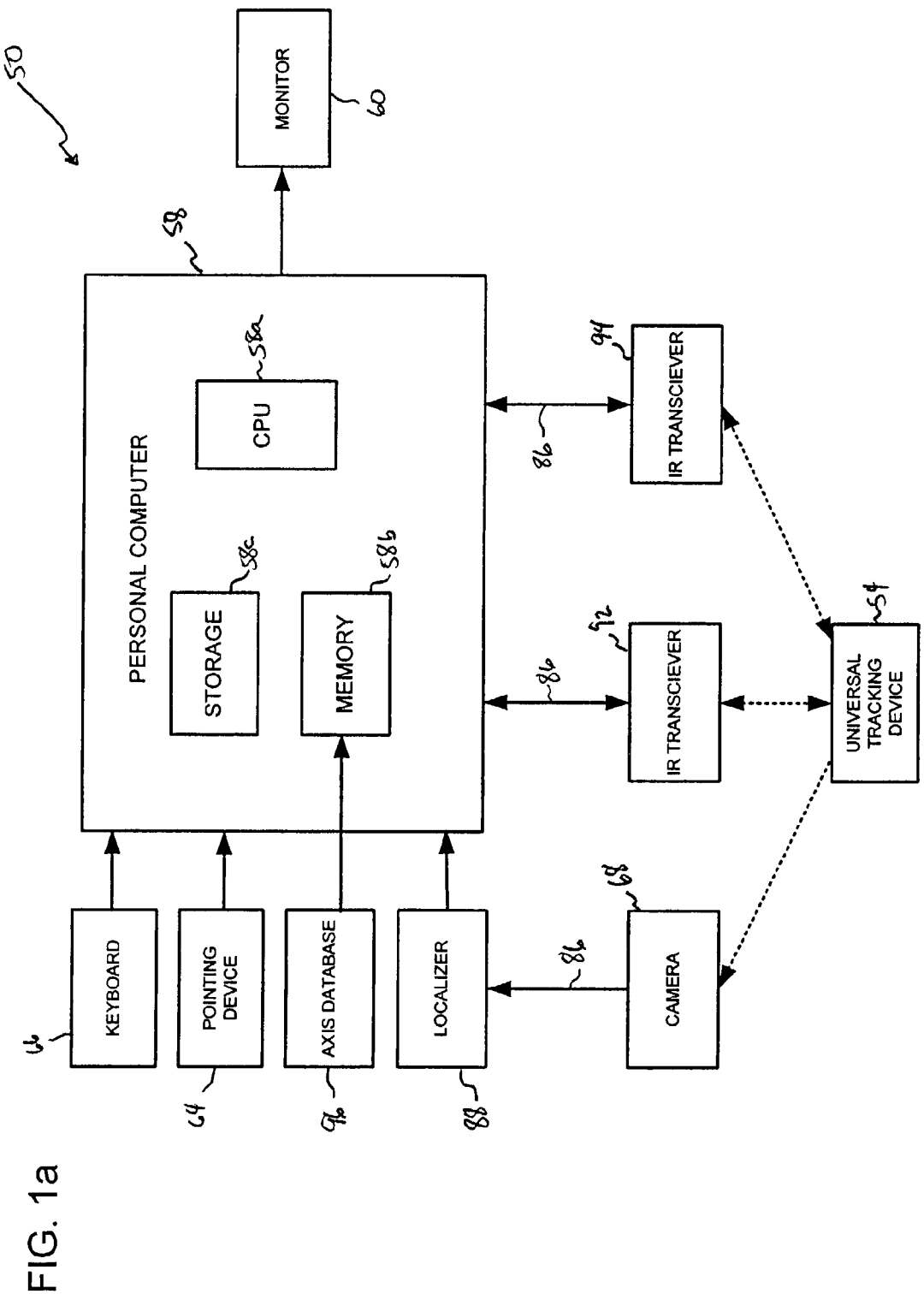
FIG. 1*a* is a block diagram of the surgical navigation system of FIG. 1.

FIGS. 1 and 1a are a schematic view and block diagram of a surgical navigation system 50 adapted to track surgical tool 52 having a universal tracking device 54 associated therewith using an adapter 56. The surgical navigation system 50 includes a computer 58, which can be any type of high-speed personal computer having a CPU 58a, a memory unit 58b, and a storage unit 58c, such as a laptop computer, as shown, or a desktop computer (not shown). If the desktop computer is used, it can be housed inside a cart 62. Mounted on the cart 62 is a monitor 60, which is attached to a video output of the computer 58. Also associated with the computer 58 are a mouse 64 or another suitable input pointing device and a keyboard 66. The surgical navigation system 50 includes a camera 68 which is comprised of three separate CCD cameras 70, 72 and 74, which cameras are adapted to detect infrared signals (IR) generated by the universal tracking device 54. The camera 68 is mounted on cart 60 by a camera arm 76. While the camera 68 is shown mounted in association with the cart 62 in FIG. 1, it is not necessary that the camera actually be physically mounted on or attached to cart 62. The camera 68 can be mounted in any stationary position such that the camera 68 has a good line of sight to the operating field in the operating room. For instance, the camera 68 can be mounted on a wall of the operating room (not shown) or can be mounted on the operating room light (not shown). Camera arm 76 also can include cable 86 from the camera 68 to a localizer 88 which is located within cart 62. The localizer 88 cooperates with the camera 68 to identify the locations of the LED's 84 on the universal tracking device 54 and any other tracking devices that may be within the field of view of the camera 68. The CCD cameras 70, 72, and 74 contain their own calibration information and transmit the position data from the LED's 84 to the localizer 88. The localizer 88 then converts the raw position data into position and orientation data using techniques that are to those of skill in the art. The localizer 88 communicates the position and orientation data to the computer 58 through cable 90. The camera 68 also includes two transceivers 92 and 94 capable of communicating with the universal tracking device 54 using techniques that are well-known to those of skill in the art. The transceivers 92 and 94 are directly connected to computer 58 through a separate circuit in cable 86. Also shown is a reference tracking device 78 attached to operating room table 80 by a tracker mount 82. While it is preferred that the reference tracking device 78 is stationary, the reference tracking device 78 could be mounted to a patient (not shown) or could be a second hand held tracking device. Both the reference tracking device 78 and the universal tracking device 54 have multiple LED's 84 that emit light in the infrared region that can be detected by CCD cameras 70, 72 and 74. A more detailed description of surgical navigation system 50 is contained in U.S. patent application Ser. No. 09/764,609 filed Oct. 21, 2001, the disclosure of which is hereby incorporated by reference.

Figure 2:
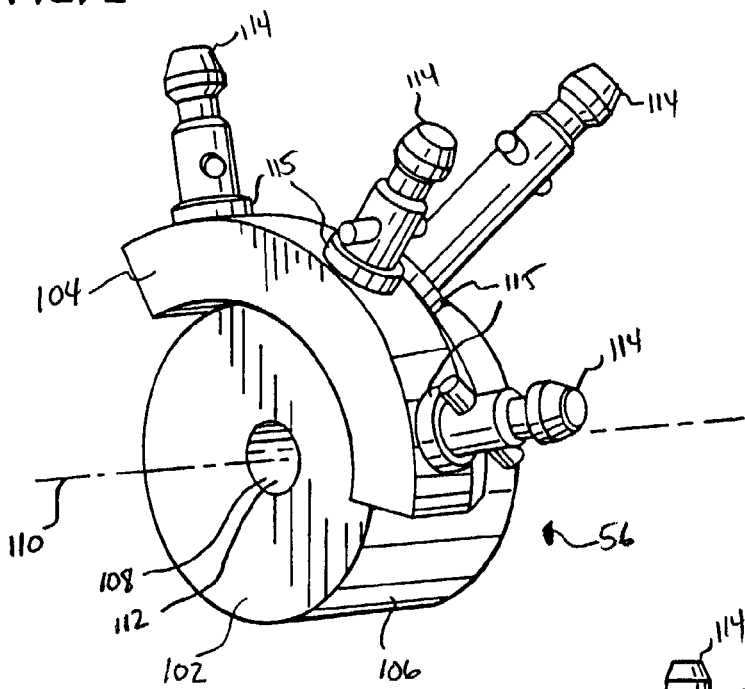
FIG. 2 is an isometric view of the adapter according to the present invention.
Figure 3:
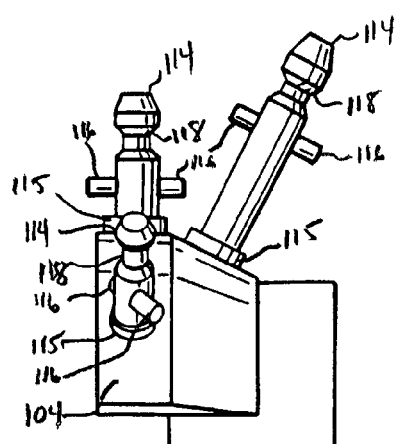
FIG. 3 is a side elevational view of the adapter of FIG. 2.
Figure 4:
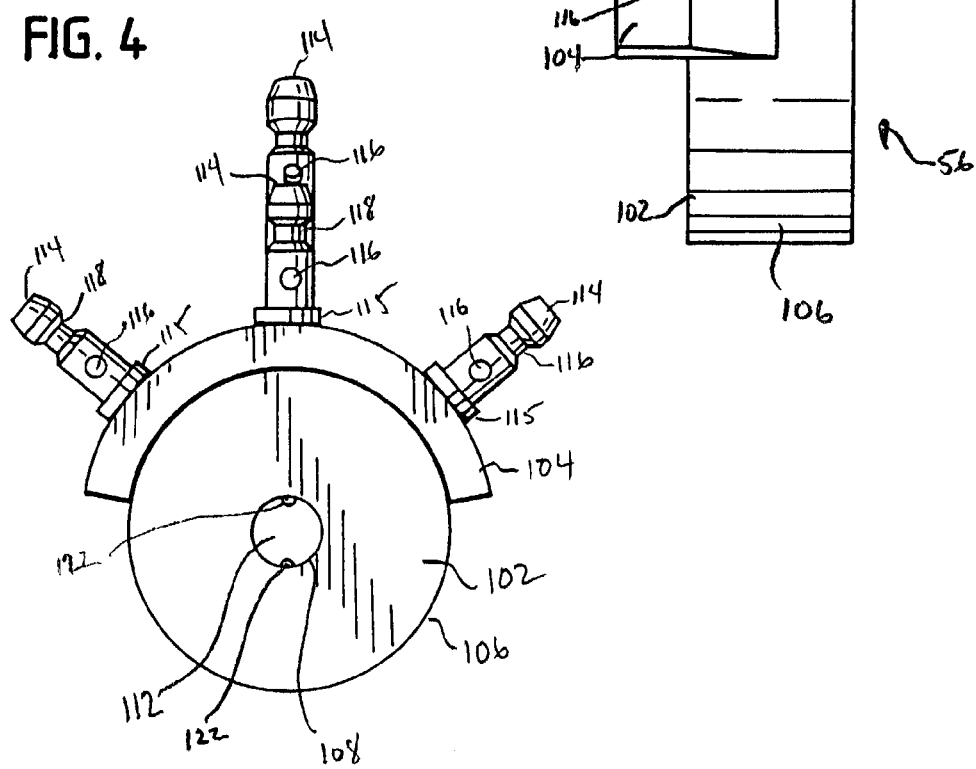
FIG. 4 is an end elevational view of the adapter of FIG. 2.
Figure 5:
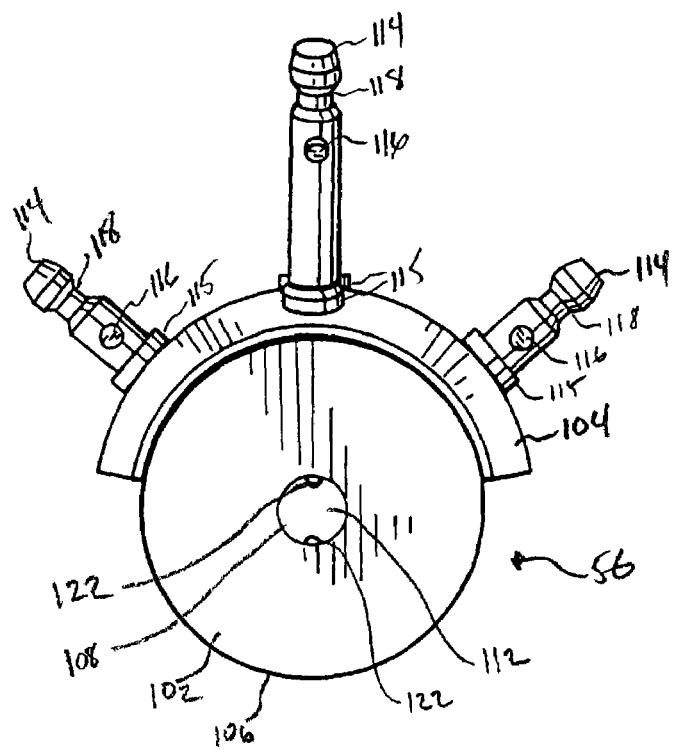
FIG. 5 is an end elevational view of the adapter of FIG. 2 from the end opposite FIG. 4.

With reference to FIGS. 2–7, the adapter 56 includes a body 102 having a docking pin bridge 104. The body 102 has an exterior surface 106 and an interior surface 108. An opening 112 is defined by the interior surface 108 and passes through the body 102. The opening 112 has an axis 110, as shown in FIG. 2. The axis 110 must have a known relation to the interior surface 108 of the adapter 56.

Multiple docking pins 114 are mounted on docking pin bridge 104. In the embodiment as shown in FIGS. 2–7, four docking pins 114 are shown. The multiple docking pins 114 are provided to enable a surgeon to mount the universal tracking device 54 on the most appropriate docking pin 114 so that during the surgical procedure to be performed the LED's 84 in the universal tracking device 54 can readily maintain a line of sight to the camera 68. While four docking pins 114 are shown in the embodiment of FIGS. 2–7, any suitable number of docking pins can be included. The docking pins 114 include a base 115, which is firmly secured to docking bridge 104 in such a manner that the docking pin 114 does not move once it has been secured to docking bridge 104. The docking pin 114 also includes two pins 116 and an undercut 118, which interact with the docking surface of the universal tracking device 54 as will be discussed in more detail hereafter to hold the universal tracking device 54 firmly to the adapter 56.

The opening 112 passes completely through the body 102 and is formed such that when a surgical tool 52 is placed through the opening 112, a tool axis 120 of the surgical tool 52 will be identical to the axis 110 of opening 112. This identity of the axis 110 and the tool axis 120 is an important aspect of the adapter 56. It enables the adapter 56 to be used with the reference tracking device 78 to calibrate not only the position of a tool tip 126 of surgical tool 52 but also calibrate the tool axis 120 such that surgical navigation system 50 can track both the position and the orientation of the surgical tool 52. The opening 112 and its axis 110 can be off set from the center of the body 102 if the surgical tool 52 is to be nonrotably held by the adapter 56.

Once the adapter 56 is placed on the surgical tool 52, it is important that the position of the adapter 56 relative to the tool tip 126 and the tool axis 120 remain undisturbed. While it is possible that the adapter 56 may be configured to rotate in place about the tool axis 120, so long as the distance from the tool tip 126 to the location of the universal tracking device 54 remains unchanged and so as long as the relation between the universal tracking device 54 and the tool axis 120 of the tool remains unchained, the position and orientation of the surgical tool 52 can be calibrated and tracked by the surgical navigation system 50.

In order to maintain the adapter 56 in a fixed location relative to the tool tip 126, spring-loaded balls 122 are provided within the interior of opening 112 and the interior surface 108 of body 102. These balls 122 are biased outwardly by springs 124 and cooperate to firmly engage the surgical tool 52 so that the relationship between the adapter 56 and the surgical tool 52 is maintained. For instance, the surgical tool 52 may have a small channel (not shown) within which balls 122 rest thereby holding the adapter 56 in a fixed relation with regard to the tool tip 126. Other means of firmly attaching the adapter 56 to the surgical tool 52 can also be used.

Figure 8:
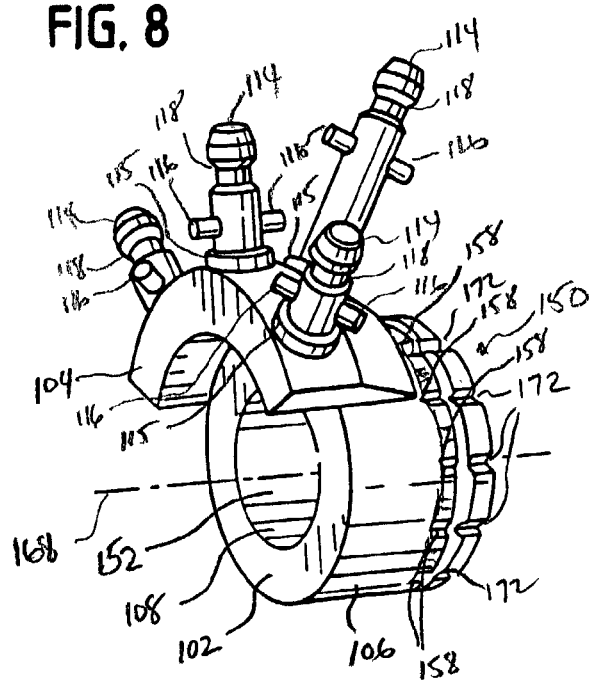
FIG. 8 is an isometric view of an alternative embodiment of the adapter of the present invention.
Figure 9:
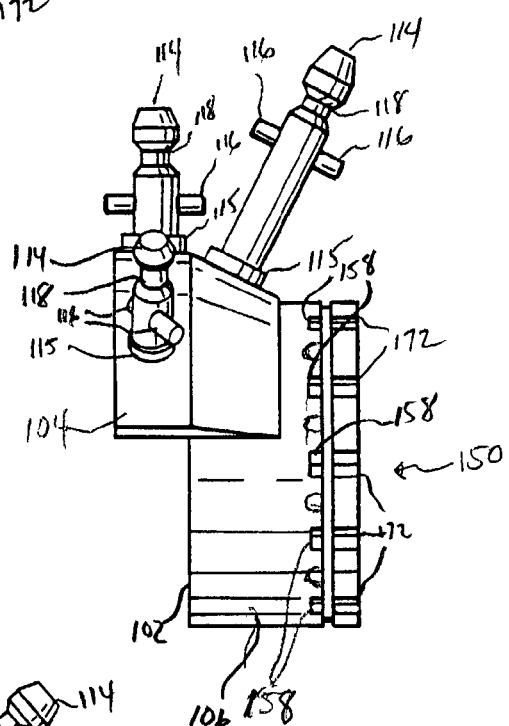
FIG. 9 is a side view of the adapter of FIG. 8.
Figure 10:
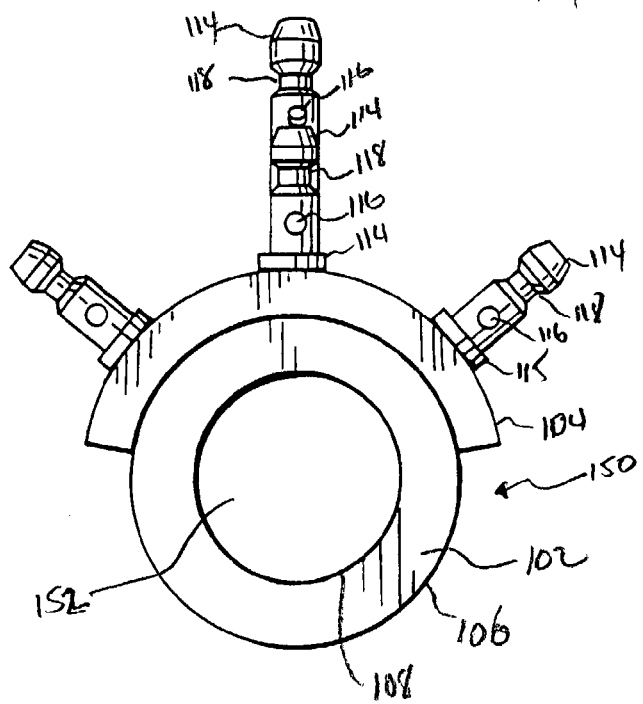
FIG. 10 is an end view of the adapter of FIG. 8.
Figure 11:
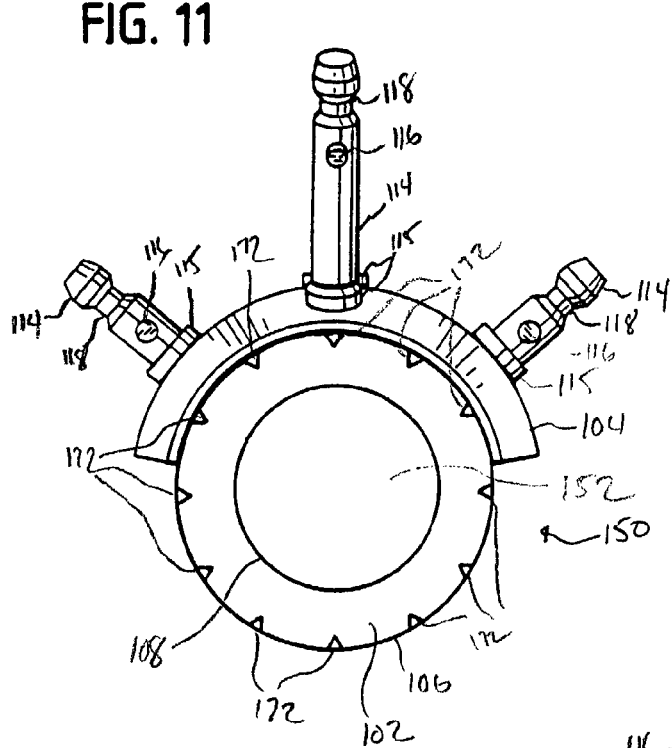
FIG. 11 is an end view of the adapter of FIG. 8 from the end opposite FIG. 10.

As shown in FIGS. 8–13, a second embodiment of the adapter 56 is shown. In describing FIGS. 8–13 similar structure will be described using the same reference number as above. An adapter 150 includes the docking pin bridge 104 and has the exterior surface 106 and the interior surface 108. As shown in FIG. 8, an axis 168 passes through an opening 152 defined by the interior surface 108. The opening 152 in the adapter 150 is larger than the opening 112 of the adapter 56. The reason for this larger opening is to interact with an attachment device 154 mounted on a surgical tool 156. On the exterior surface 106 of the adapter 150 are a series of detents 158. Detents 158 interact with a series of balls 160 held within an interior surface 162 of the attachment device 154. These balls 160 are held in place by a locking ring 164 that encircles the exterior of the attachment device 154. The attachment device 154 also includes a smooth protrusion 166 that is shaped so that it closely interfits with the opening 152 of the adapter 150. The shape of the smooth protrusion 166 is such that the axis 168 of the opening 152 is in identity with a tool axis 170 of the surgical tool 156. In addition, a series of grooves 172 are shown on the exterior surface 106 of the adapter 150. These grooves are arranged around the end of the adapter 150 opposite the docking pin bridge 104. These grooves 172 interact with one or more pins 174 in a back surface 176 of the attachment device 154. The grooves 172 and the pins 174 keep the adapter 150 from rotating about the axis 168. Either or both of grooves 172 or pins 174 can be omitted if it is desired that the adapter 156 be able to rotate freely about the axis 168.

Figure 6:
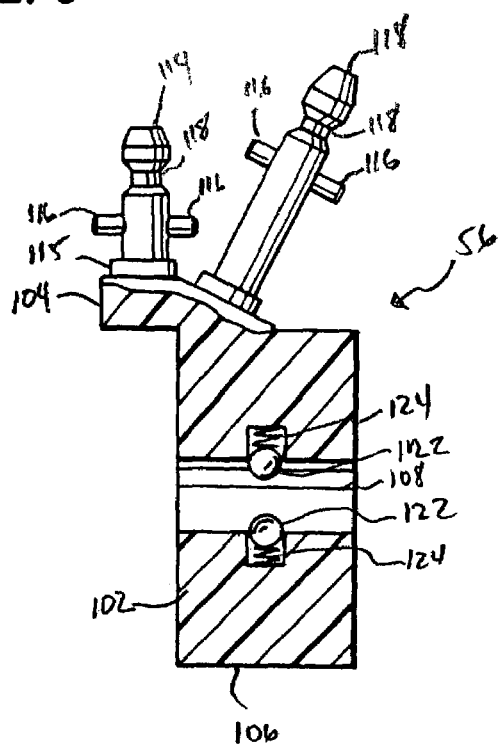
FIG. 6 is a sectional view of the adapter of FIG. 2 taken generally along the line 6—6.
Figure 7:
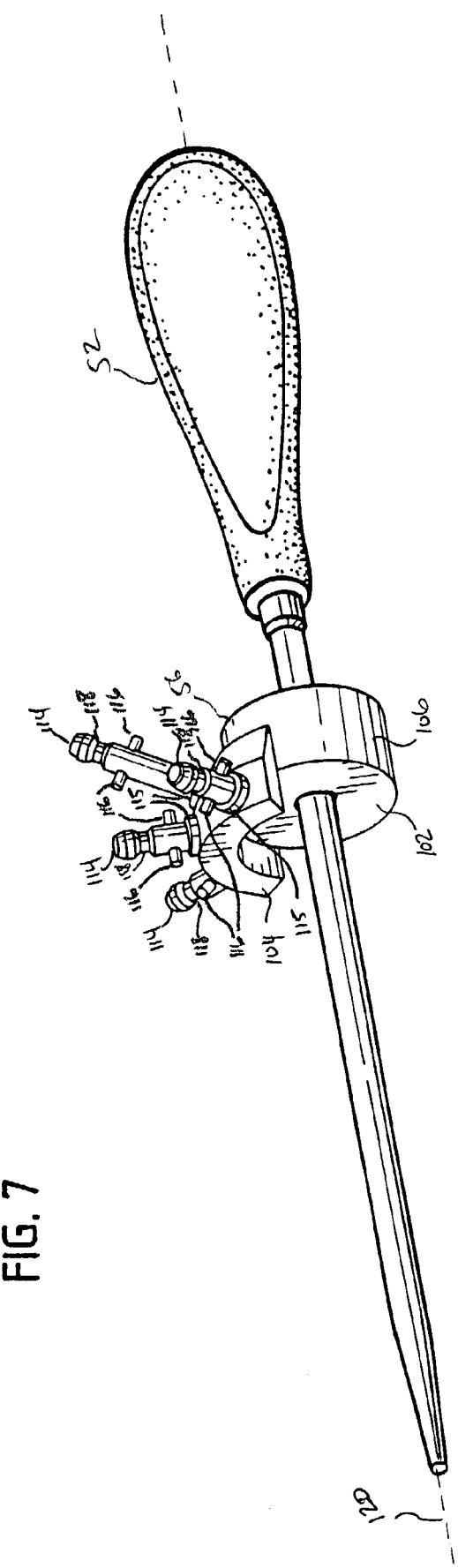
FIG. 7 is an isometric view of the surgical tool with the adapter in place.
Figure 12:
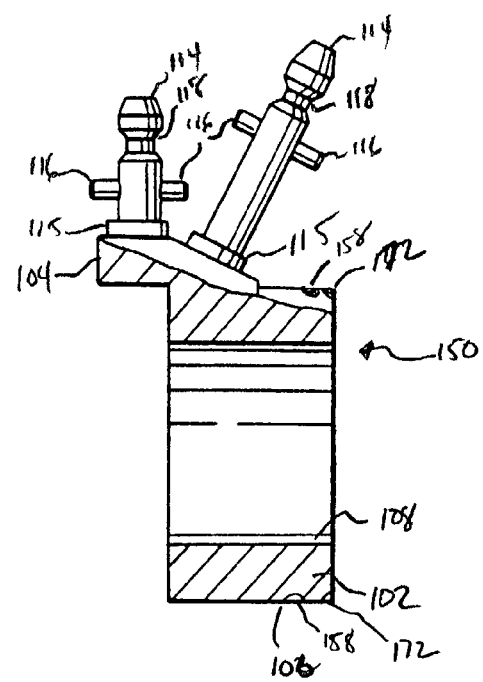
FIG. 12 is a sectional view the adapter of FIG. 8 taken generally along the lines 11—11.

As shown in FIGS. 6 and 12, the adapters 56 and 150 of the present invention be made from any suitable material that is dimensionally stable and capable of being sterilized at least one time. Though it may be desirable that the adapter be capable of being repeatedly sterilized, it is also possible that the adapters of the present invention are designed as disposable single use items, which are sterilized upon manufacture, maintained in a sterile condition until use and then discarded. As shown in FIG. 6, suitable plastics, which are dimensionally stable and surgically acceptable, such as polyetheretherketone (PEEK), carbon fiber reinforced PEEK, polysulfone, polycarbonate, nylon and mixtures thereof, can be used. In addition, as shown in FIG. 12, suitable metals that are acceptable for use in surgery such as surgical stainless steel, titanium, tungsten carbide and other similar surgically suitable metals can be used.

Figure 14:
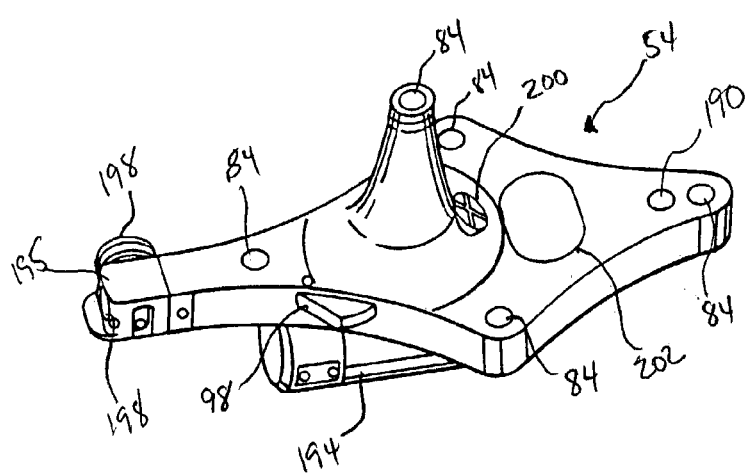
FIG. 14 is an isometric view of a surgical tool to be used with the adapter of FIG. 8.
Figure 13:
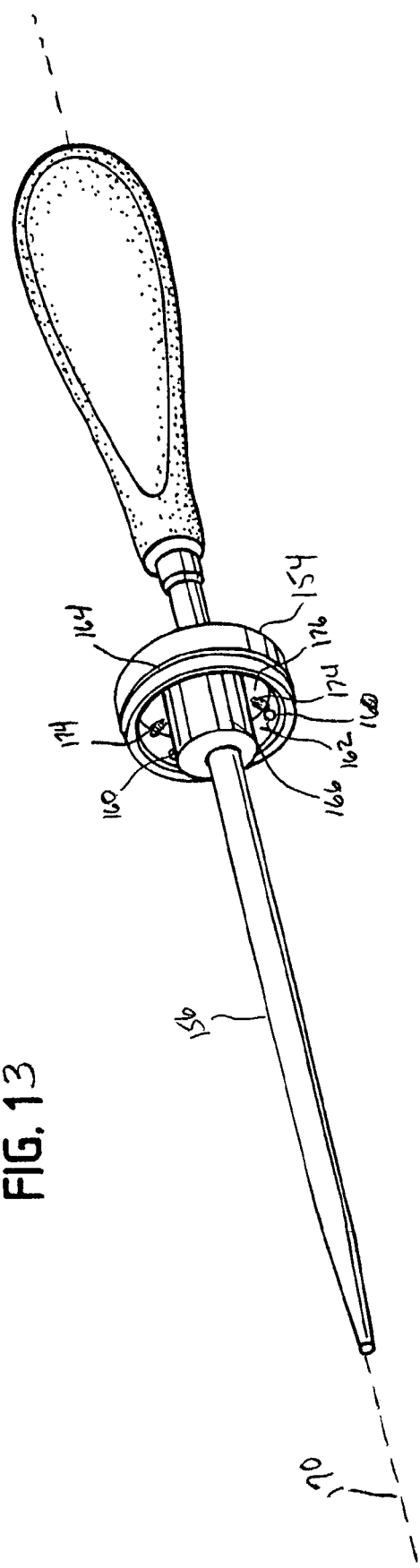
FIG. 13 is an isometric view of a universal tracking device.

Turning now to FIG. 14, the universal tracking device 54 is shown in more detail. The universal tracking device 54 as shown in FIG. 14 includes five LED's 84, which are arranged such that no three LED's lie in a single line. This arrangement enables the surgical navigation system 50 to determine both the position and the orientation of the universal tracking device 54. As stated previously, these LED's 84 typically emit light in the infrared region as is well known to those of ordinary skill in the art. The universal tracking device 54 has a button 98. This button 98 activates the LED's 84 so that the camera 68 of the surgical navigation system 50 can locate the universal tracking device. The universal tracking device 54 also includes a status light 190 which can be programmed to operate in a variety of ways. For instance, the status light 190 can be programmed so it is illuminated for a short period of time after a power source such as a battery 194 is inserted into a suitable battery holder in the universal tracking device 54. The universal tracking device 54 also includes a zero tolerance adapter interface 195, which includes an opening 196 through which one of the docking pins 114 can be inserted. The structure of the opening 196 and the docking pins 114 are such that when the docking pin 114 is inserted through the opening 196, an internal lock (not shown) snaps around undercut 118. The internal lock can be released by pressing a button 198 to remove the universal tracking device 54 from the docking pin 114. The importance of the zero tolerance nature of the adapter interface is that once that the universal tracking device 54 is placed upon the docking pin 114, the relative position of the universal tracking device 54 and the docking pin 114 must not be disturbed. Once the composite universal tracking device 54, adapter 150 and surgical tool 156 is calibrated, the surgical tool 156 can be tracked by the surgical navigation system 50. However, if the relation among these components is disturbed, the composite unit must be recalibrated.

In addition, the universal tracking device 54 also includes a calibration point 200. The calibration point 200 is in a known relation to LED's 84 and has a center point that is easily identified so that the universal tracking device 54 can be used also as a reference tracking device 78, as shown in FIG. 1. In addition, the universal tracking device 54 includes a communication transceiver 202 that enables the universal tracking device to communicate directly with the surgical navigation system 50 through the transceivers 92 and 94.

Figure 15:
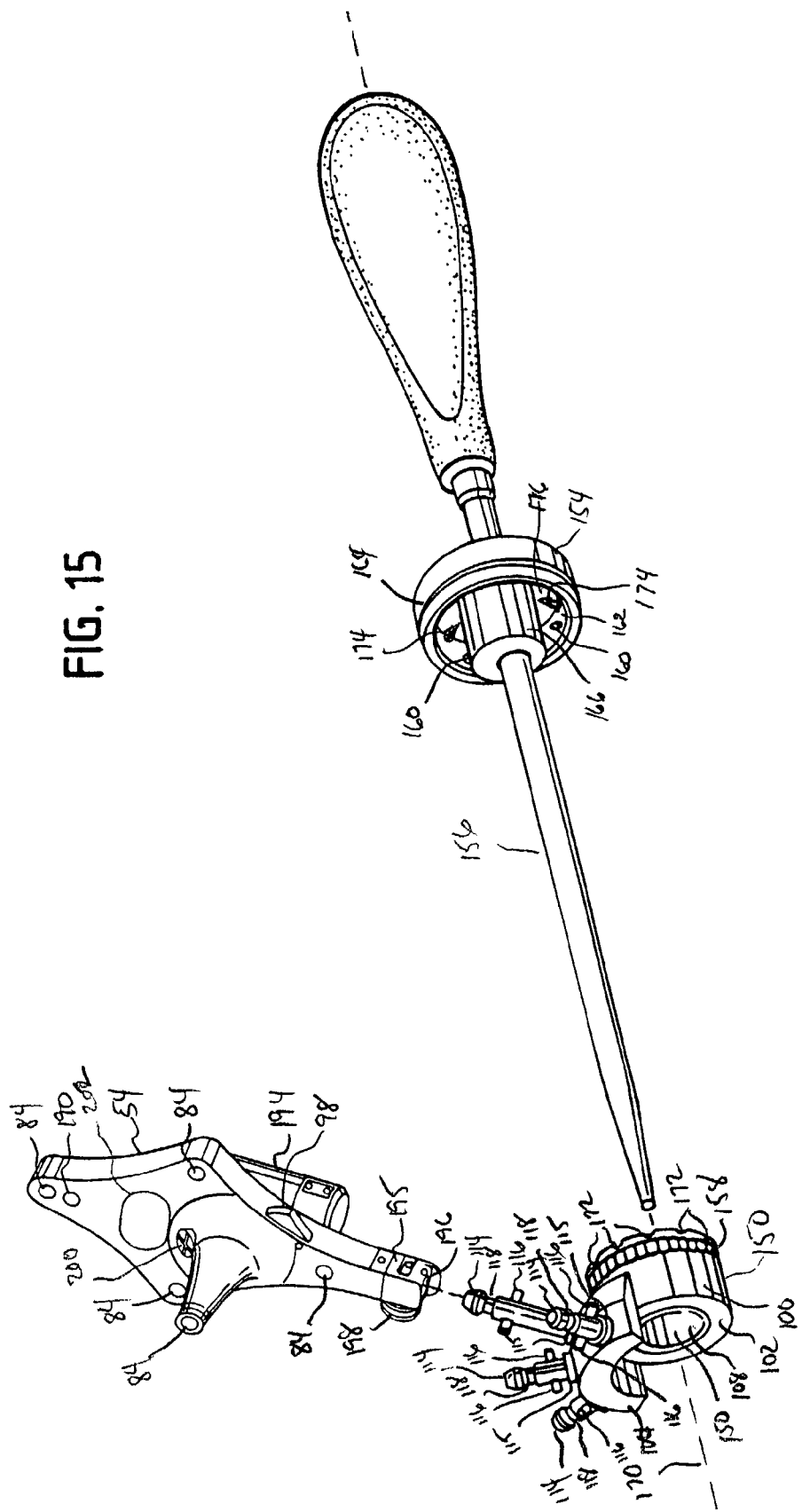
FIG. 15 is exploded view of the adapter of FIG. 8, the surgical tool of FIG. 14, and the universal tracking device of FIG. 13.
Figure 16:
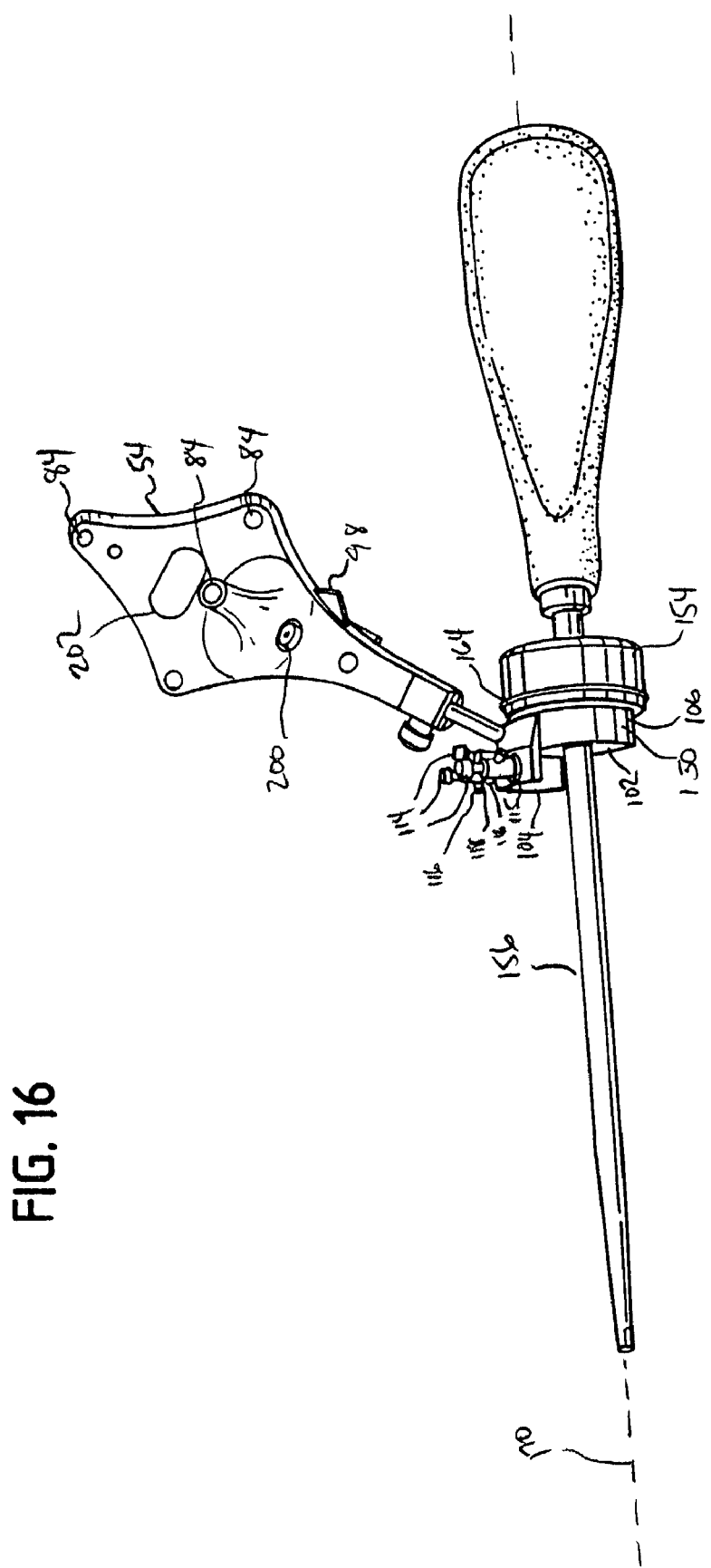
FIG. 16 is an assembled view of the adapter of FIG. 8, the surgical tool of FIG. 14, and the universal tracking device of FIG. 13.

FIG. 15 shows an exploded view of the universal tracking device 54, the adapter 150, and the surgical tool 156. In use, the adapter 150 is slid along the length of the surgical tool 156 until the adapter 150 firmly engages attachment device 154, which is firmly attached to the surgical tool 156. Typically the attachment device 154 is formed along with the surgical tool 156 during the manufacture but it is also possible to retrofit the attachment device 154 onto the surgical tool 156 by means of a suitable attachment means (not shown). In FIG. 16, a view of the surgical tool 156, the adapter 150, and the universal tracking device 54 in an assembled configuration is shown. As noted previously, the surgical tool 156 and the attached universal tracking device 54 must be calibrated before it can be used with the surgical navigation system 50.

Figure 17:
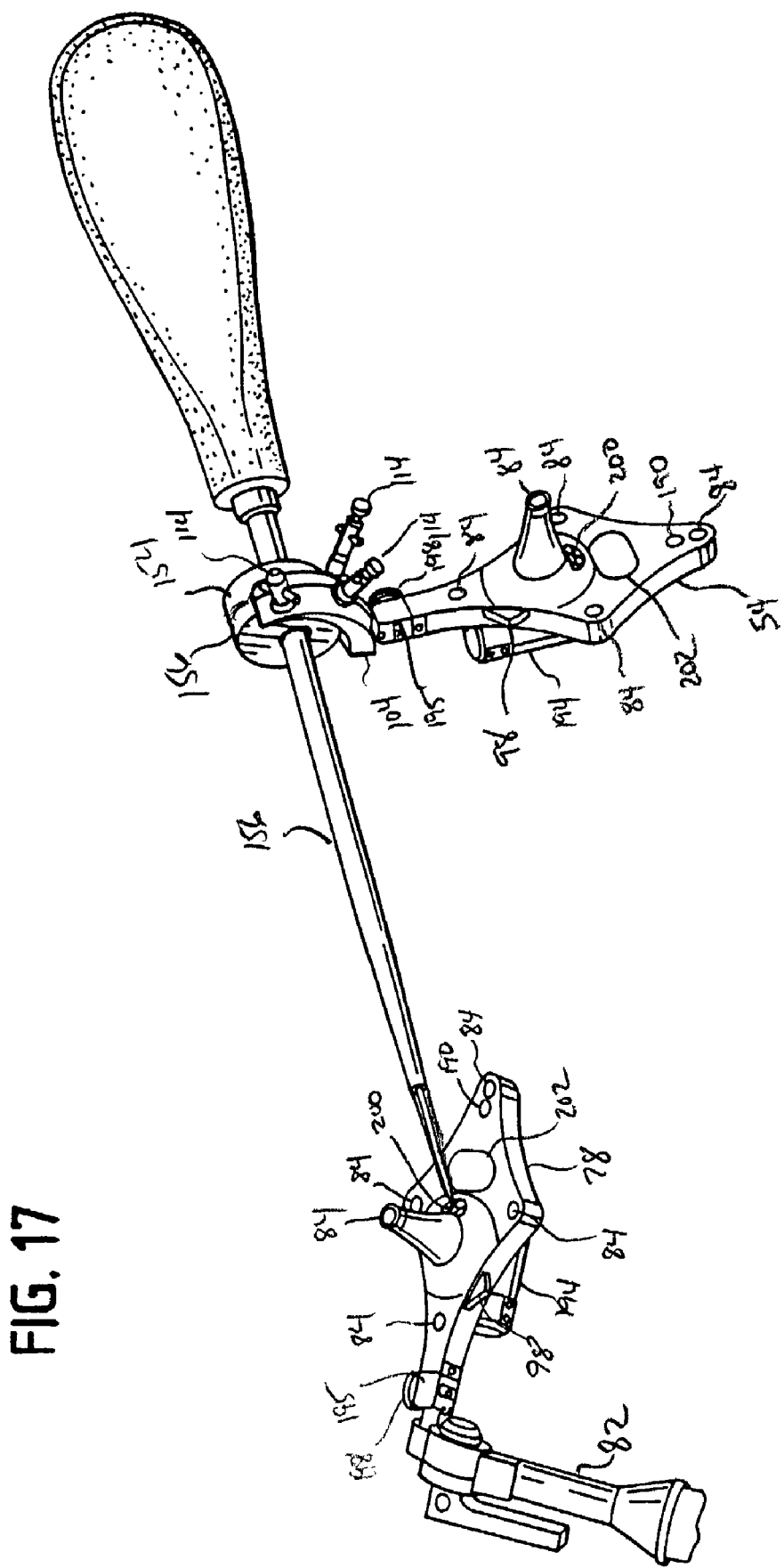
FIG. 17 is a view of the calibration device showing the surgical tool of FIG. 14 with the adapter of FIG. 8 and the universal tracking device of FIG. 13 touching the calibration point.

As shown in FIG. 17, the tool tip 126 is placed against the calibration point 200 of the reference tracking device 78. Both the location of the calibration point 200 on the reference tracker device 78 and the position of universal tracking device 54 are known to the surgical navigation system 50. Because of this known relation, the surgical navigation system 50 can determine the location of tool tip 126 relative to the universal tracking device 54 as the tool tip 126 is held against the calibration point 200. The surgical navigation system 50 then stores the tool tip location and the relation of the tool tip location to the universal tracking device 54 within the memory 58b of the computer 58. In addition, the surgical navigation system 50 is able to calibrate the orientation of the surgical tool 156 because the adapter 150 is used to attach the universal tracker device 54 to the surgical tool 156. The adapter 150 has a known and previously defined relationship among the various docking pins 114 to the axis 168 of the opening 152 and to the tool axis 170. Also, the relationship between each docking pin 114 and the universal tracking device 54 is also known and previously defined. These relationships are stored within a database maintained in the memory 58b of the computer 58 for each adapter that can be used with the surgical navigation system 50.

Figure 18:
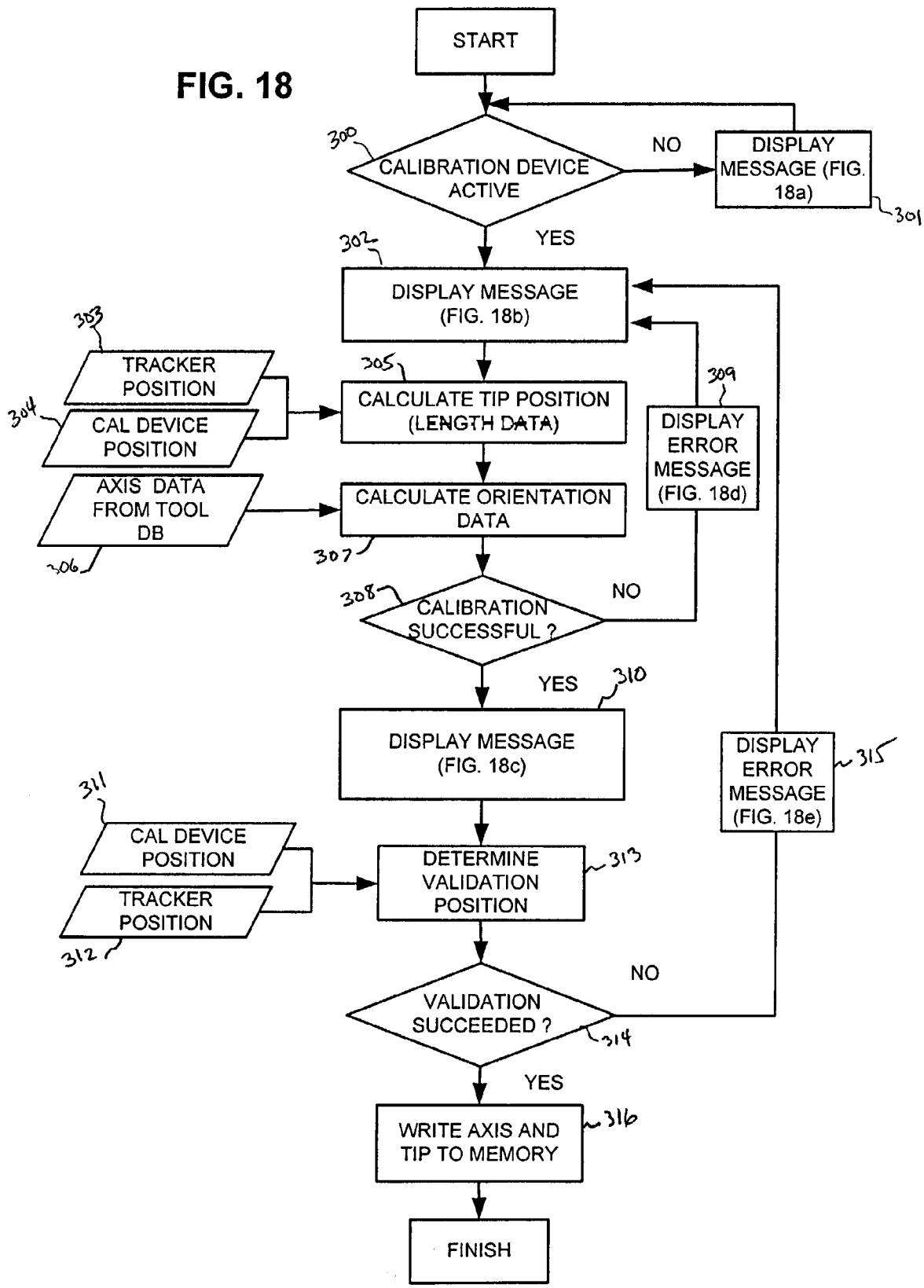
FIG. 18 is a block diagram of a computer program embodying the method of the present invention.
Figure 18A:
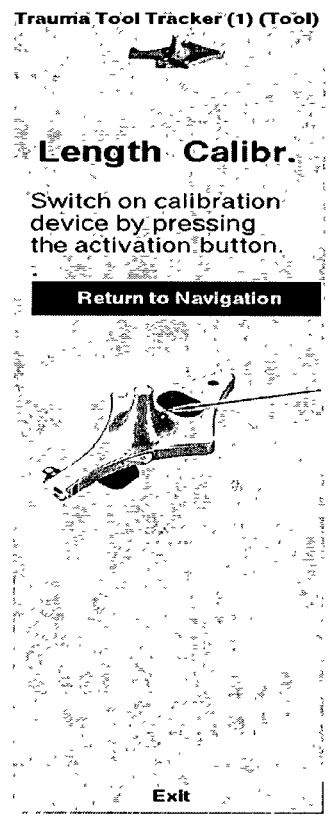
FIGS. 18*a*, 18*b*, 18*c*, 18*d* and 18*e* are representative screen shots of various messages boxes as depicted in FIG. 18.
Figure 18B:
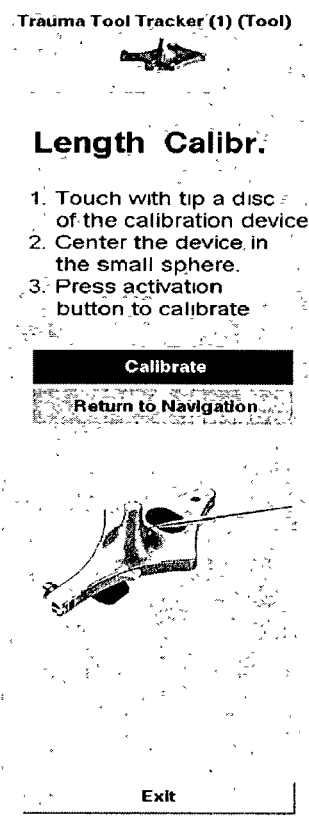

FIG. 18 is a block diagram of a computer program embodying the method of the present invention. The program begins at a block 300 which determines if a calibration device, such as the reference tracking device 78, is active. If the device is not active, the program branches to a block 301, which displays a message, as shown in FIG. 18a, that the calibration device should be switched on. The program returns to the block 300 and waits until the surgical navigation system 50 receives a signal that the calibration device has been turned on. Once the calibration device has been activated, the program then branches to a block 302, which displays a message, as shown in FIG. 18b, instructing the user first to touch the point of the tool, such as tool tip 126, to the calibration point on the calibration device, such as calibration point 200, and second to press the button on the tracking device, such as the button 98. When the button 98 is activated, the LED's 84 on the universal tracking device 54 activate and are detected by the camera 68. The portion data for the LED's 84 is sent to the localizer 88 which transmits the position and orientation of universal tracking device 54 to computer 68. This is data stored in memory 58b and is shown as a data block 303. In a similar manner, the surgical navigation system 50 determines the position and orientation of the calibration device, such as reference tracking device 78. This data is also stored in memory 58b and is shown as a data block 304. The program then proceeds to a calculation block 305. In the block 305, the program calculates the tool tip position from the stored data position of the tracking device from the data block 303 and the stored position of the calibration device in the data block 304. The calculation of the tool tip position, is done in a conventional fashion using algorithms that are well known and recognized by those of skill in the art.

The tool tip position from the calculation block 305 is then stored and the stored tool tip position is passed to a calculation block 306 that calculates the orientation data for the surgical tool 156. In addition to the tool tip position from the block 305, surgical navigation system 50 has the database 96 of possible axes for the opening 152 relative to location of the universal tracking device 54 stored in memory 58b in the database 96. The database 96 is shown as a data block 306 and contains data previously stored in memory 58b relative to the relative position of the universal tracking device 54 relative to the possible axes of the opening for various adapters, such as axis 110 or axis 168. Since the adapter 56 and the adapter 150 can have a number of different docking pins 114, each of these docking pins is in a different position and orientation relative to the axis 110 and axis 168, respectively. The relative position of the universal tracking device 54 to either the axis 110 or the axis 168 for each docking pin 114 can be calculated by methods well known in the art. The result of this calculation for the location each docking pin 114 for each possible adapter that can be used with the surgical navigation system 50 is stored in the database 96 which has been previously loaded into in the memory of computer 58b on initialization of the program.

Figure 20:
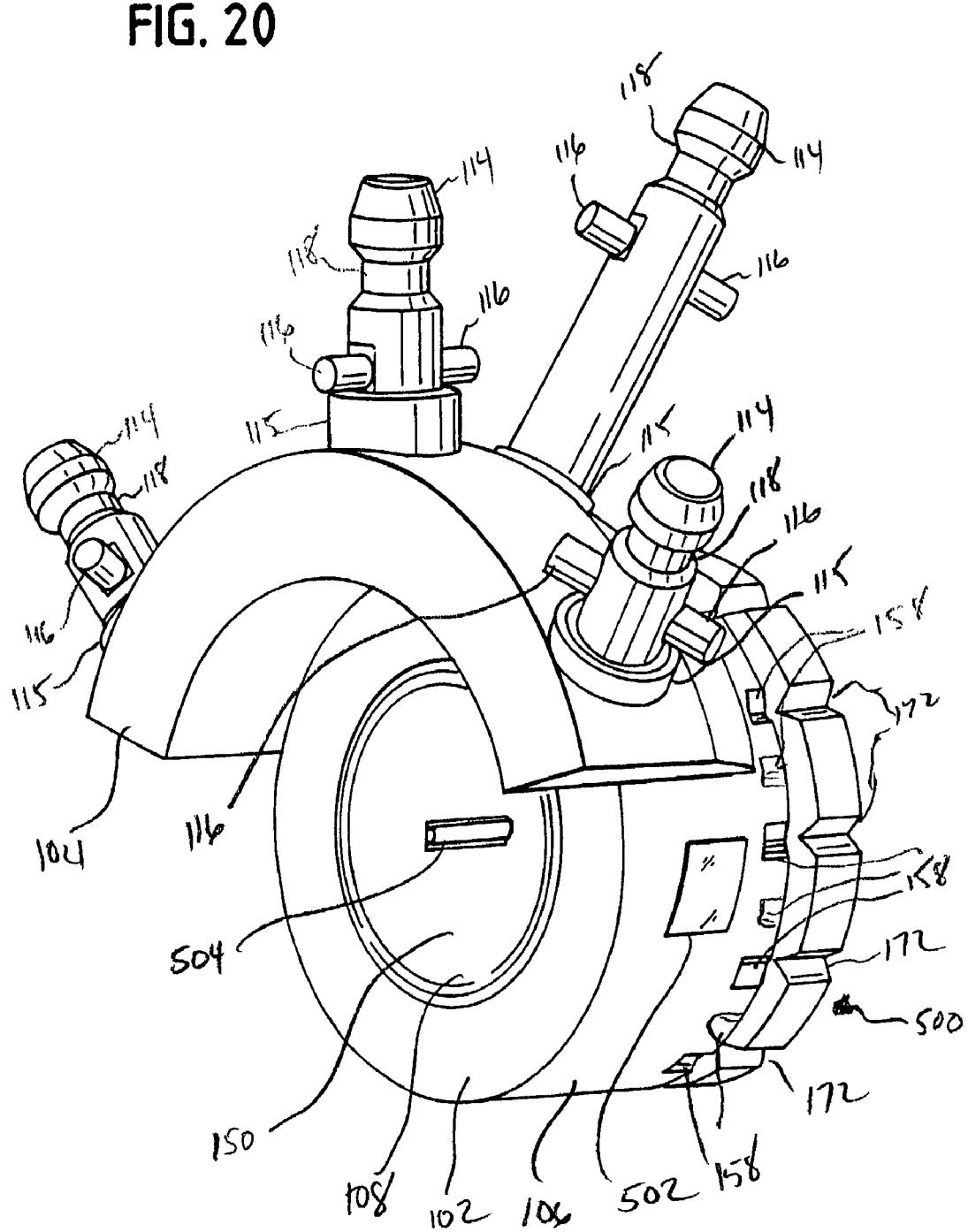
FIG. 20 is an isometric view of a further embodiment of the adapter similar to that shown in FIG. 8.

As there can be number of different adapter configurations, the distance from the universal tracking device 54 to the axis of each particular adapter will vary. Each type of adapter can be encoded with a specific identifier that can be entered into the surgical navigation system 50. This can be done manually using the keyboard 66 or the mouse 64 to indicate which adapter is being used or automatically using a smart adapter 500 as shown in FIG. 20. The adapter 500 has a communication transceiver 502 which is capable of transmitting information stored in the adapter 500, such as a particular model number and/or style number, to the surgical navigation system 50 through communication transceivers 92 and 94.

Once the surgical navigation system 50 knows the identity of the particular adapter, the database 96 is queried for the potential axis for the particular adapter being used, such as the adapter 150, and the subset of the data is placed in memory as indicated by the data block 306 along with the tool tip position from the block 305. The subset of data stored in the data block 306 from database 96 is then used to calculate the orientation data. The program proceeds to a block 307, which calculates the orientation data by comparing the tool tip position with the data subset that has been taken from database 96 stored in the data block 306 for that particular adapter. If the tool tip position is located along any of the potential axes from the data block 306 and if the deviation of the tool tip position from the chosen potential axis is within acceptable limits, then the program branches, as shown in a block 308, to the validation process. If the position of the tool tip is not on one of the axes within acceptable limits, the program branches to block 309 that displays an error message as shown in FIG. 18d. Control then loops back to the block 302 to repeat the calibration process.

Figure 18C:
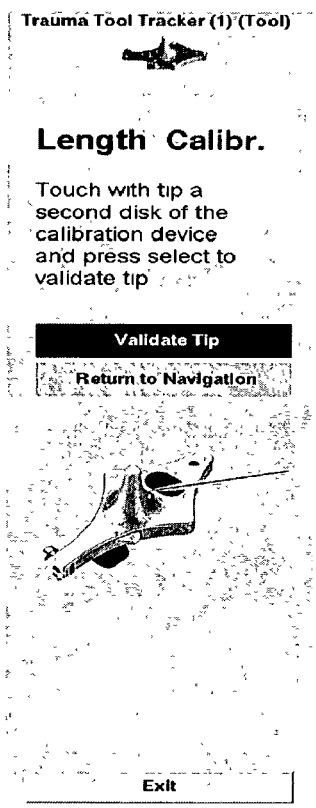
Figure 18D:
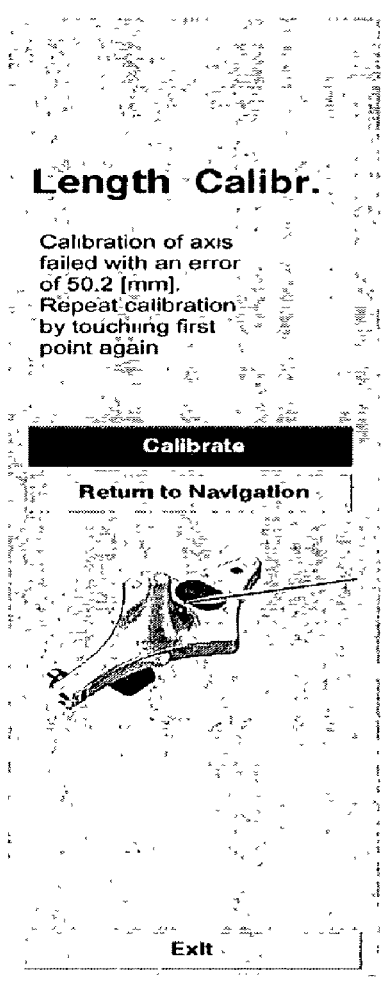
Figure 18E:
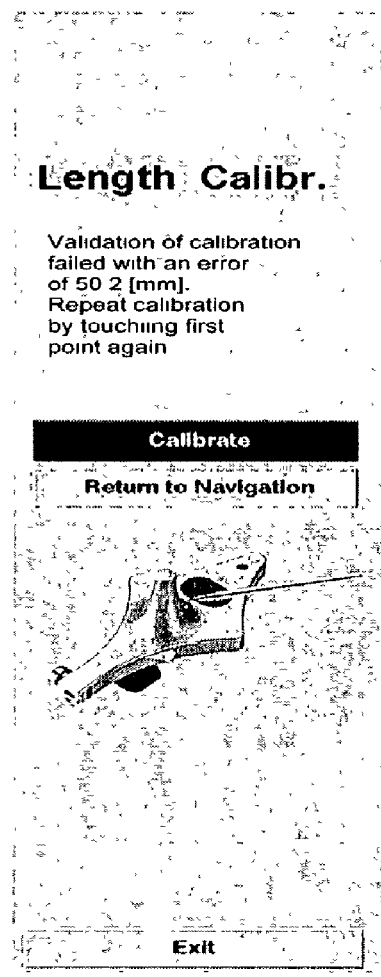

At the beginning of the validation process, a block 310 displays a message as shown in FIG. 18c. The message instructs the user to touch the tool tip to the calibration point 200 of the calibration device, and then to press the button 98. Once the button 98 is pressed, the surgical navigation system 50 determines the position of the universal tracking device 54 as described above and stores the position in a data block 312. Also, the position of the calibration device is determined in the same manner as above and a data block 311 stores the position of the calibration device. A block 313 then compares the position stored in the data block 311 with the stored tool tip position from the block 305. If the comparison by the block 313 is within acceptable error limits, a block 314 determines whether the calibration has been validated and the axis data and the tool tip position data are then written into memory 58b as indicated by block 318. If the validation process does not succeed, i.e., if the comparison is greater than the acceptable error, then the program branches and a block 315 displays the message as shown in FIG. 18e that instructs the user to repeat the calibration step. At any time during either the calibration or validation step, the user has the option to cancel the entire process and either begin calibration again or return to another task.

Figure 19:
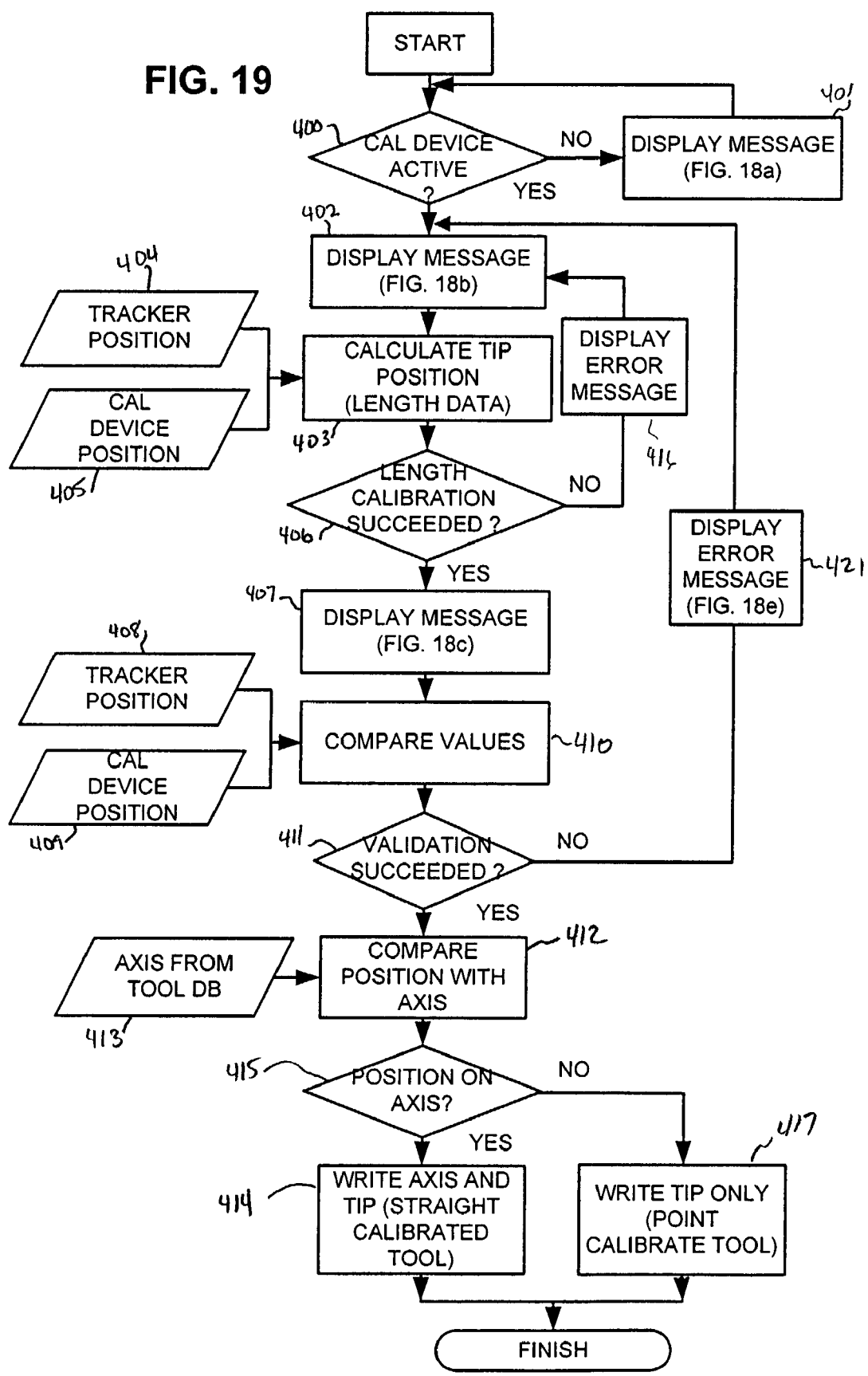
FIG. 19 is a block diagram of a computer program of an alternative method of the present invention.

FIG. 19 shows a block diagram for an alternative method of the present invention. The program begins at a block 400 that determes if a calibration device is active. If the calibration device is not active, a block 401 displays a message and the program waits until a calibration device is activated. The message displayed in the block 401 is similar to that shown in FIG. 18a. After a calibration device is activated, a block 402 displays a message similar to that shown in FIG. 18b. Once the user touches the tool tip 126 to the calibration point 200 on the reference tracking device 78 and presses the tracker button 98 on the universal tracking device 54, a block 403 calculates the tool tip position using the data generated from the position of the universal tracking device 54 stored in a data block 404, and the data on the position of the calibration device stored in a data block 405. The tool tip position is calculated by the block 403 in a manner similar to that described in reference to FIG. 18. Once the tool tip position has been determined and stored, a block 406 determines whether or not the calibration step has been successfully completed. If the calibration step did not succeed, for instance, if one of the tracking devices was not visible to the surgical navigation system 50, a block 416 displays an error message indicating the nature of the error.

If the calibration is concluded, the block 406 stores the tool tip position in memory, the program precedes to a block 407 that displays the validation message that is similar to that shown in FIG. 18c. The message instructs user to touch the tool tip 126 to the calibration point 200 on reference tracker device 78 and then press the activation button 98 on the universal tracking device 54. As the tracking device is activated, a block 408 determines and stores the tracking device position and a block 409 determines and stores the calibration position in a manner similar to that described above. A block 410 then compares the validation tool tip location with the stored tool tip position. If a block 411 determines that the variation between the tool tip position stored in the block 403 and the validation value determined by the block 410 is greater than an acceptable limit, the validation is not successful and branches, as indicated in a decision, a block 421 displays an error message. This error message will be similar to that shown in FIG. 18e. On the other hand, if the comparison in block 410 is within acceptable error limits then the block 411 sends control to the axis calibration.

A block 412 determines axis calibration by taking the stored validated tool tip position from the block 410 and determining whether or not this tool tip position lies on any of the available axes stored in a block 413 from the axis database. The axis database is similar to that described relative to FIG. 18. The block 412 compares the validated tool tip position with the coordinates of any of the axes lines available to the system using the appropriate adapter. If the tool tip position does lie on one of the appropriate axes, that axis is chosen and a block 415 branches to a block 414 that writes the chosen axis and the tool tip position data to memory 58b to provide a fully calibrated tool. On the other hand, if the tool tip position does not lie on one of the axes in the database within acceptable limits, the block 414 branches to a block 417 that writes only the tool tip position data to the memory 58b, to create a point calibrated tool, i.e., a tool that has only its tip position calibrated but the tool orientation is not calibrated. After the appropriate data is written to memory, the calibration task is finished and then the program exits and proceeds to other tasks.

Turning now to FIG. 20, a third embodiment of the adapter of the present invention is shown. In this embodiment, the adapter 500, which is similar to the adapter 150, is provided. This adapter differs from the adapter 150 in that it has two additional features. The first additional feature is the communication transceiver 502 which enables the adapter 500 to communicate information to the surgical navigation system 50. This information may include the identity and type of the adapter so that the appropriate data from the tool axis database can be chosen without user intervention. Also, a switch 504 is shown on the interior surface 108 of the adapter 500. This switch 504 will be depressed or activated when the surgical tool 156 is inserted into the opening 152 of adapter 500. Any suitable switch can be used as the switch 504. For instance, the switch 504 could be one which when depressed sends a signal through to the communication transceiver 502 to the surgical navigation system 50 indicating that one tool 156 has been inserted into adapter 500. Similarly, as one tool is removed from opening 152 and a new device is placed into the opening 152 of adapter 500, the switch is first opened as the tool is removed and depressed as the new tool is inserted. This in turn sends a signal through the communication transceiver 502 to the surgical navigation system 50 indicating at a minimum that the state of the adapter has changed and the tool needs to be recalibrated. This may be important since the adapter could be used for a wide variety of tools during a surgical procedure, each of which would have a different length so that the distance from the universal tracking device 54 to the tool tip be different. The system then will prompt the user to recalibrate the new combination of the universal tracking device 54, the adapter 500 and the surgical tool 156 so that the correct data will be used and displayed on the monitor 60. Similarly as a tool is removed, the switch 504 will open and send a signal to the surgical navigation system 50 informing the system that there is no tool associated with that adapter and its associated universal tracking device. This will make that particular tracking device, surgical tool and adapter combination invalid for use with the system until calibration is performed.

INDUSTRIAL APPLICABILITY

The present invention is useful to quickly and easily calibrate both the position and orientation of a particular surgical tool without the need for complicated calibration devices that must be separately sterilized to be used within a surgical environment.

Numerous modifications to the present invention will be apparent to those skilled in the art in view of the foregoing description. Accordingly, this description is to be construed as illustrative only and is presented for the purpose of enabling those skilled in the art to make and use the invention and to teach the best mode of carrying out same. The exclusive rights to all modifications which come within the scope of the appended claims are reserved.

We claim:

1. A method for calibrating a position and an orientation of a surgical tool for use with a surgical navigation system comprising the steps of:
   attaching a tracking device capable of communication with the surgical navigation system to the surgical tool using an adapter, the surgical tool having a tool axis and a tool tip, and the adapter having a known relation between the tracking device and the tool axis;
   touching the tool tip to a calibration device capable of communication with the surgical navigation system and capable of determining a position of the tool tip relative to a position of the tracking device;
   calculating the position of the tool tip;
   calculating orientation data for the surgical tool from the known relation between the tracking device and the tool axis and from the position of the tool tip; and
   storing the position of the tool tip for the surgical tool and the orientation data for the surgical tool within memory of the surgical navigation system so that when the surgical tool is used with the surgical navigation system, the position and the orientation of the surgical tool can be tracked by the surgical navigation system.

2. The method of claim 1 wherein the adapter has an interior surface and the interior surface defines an opening having an axis and the known relation is identity of the tool axis and the axis of the opening.

3. The method of claim 1 wherein the tracking device is attached to the adapter by a docking structure.

4. The method of claim 1 wherein the docking structure locks the tracking device into a specified position with respect to the adapter.

5. The method of claim 1 wherein the surgical navigation system is an optical system.

6. The method of claim 1 including the additional step of communicating identity information from the tracking device to the surgical navigation system.

7. The method of claim 1 including the additional step of determining the presence of a surgical tool in the adapter.

8. The method of claim 1 including the additional step of communicating the presence of the adapter to the surgical navigation system.

9. The method of claim 1 including the additional step of validating the position of the tool tip.

10. The method of claim 1 including the additional steps of providing a database of known relations of the tracking device to the tool axis; and using the database and the position of the tool tip to calculate the orientation data for the surgical tool.

11. A method for calibrating a position and an orientation of a surgical tool for use with a surgical navigation system comprising the steps of:

attaching a tracking device capable of communication with the surgical navigation system to the surgical tool using an adapter, the surgical tool having a tool axis and a tool tip, and the adapter having a known relation between the tracking device and the tool axis;

touching the tool tip to a calibration device capable of communicating with the surgical navigation system and capable of determining a position of the tool tip relative to a position of the tracking device;

calculating the position of the tool tip;

storing the position of tool tip within memory of the surgical navigation system; and determining orientation data for the surgical tool from the position of the tool tip and from a database of stored relations of the tracking device to the tool axis and from the position of the tool tip, such that the position of the tool tip intersects an axis of the surgical tool from the database, so that when the surgical tool is used with the surgical navigation system the position and the orientation of the surgical tool can be tracked by the surgical navigation system.

12. The method of claim 11 wherein the adapter has an interior surface and the interior surface defines an opening having an axis and wherein the tool axis of the surgical tool inserted within the opening and the axis of the opening are identical.

13. The method of claim 11 wherein the tracking device is attached to the adapter by a docking structure.

14. The method of claim 11 wherein the docking structure locks the tracking device into a specified position with respect to the adapter.

15. The method of claim 11 wherein the surgical navigation system is an optical system.

16. The method of claim 11 including the additional step of communicating identity information from the tracking device to the surgical navigation system.

17. The method of claim 11 including the additional step of determining the presence of a surgical tool in the adapter.

18. The method of claim 11 including the additional step of communicating the presence of the adapter to the surgical navigation system.

19. The method of claim 11 including the additional step of validating the position of the tool tip.

20. The method of claim 11 wherein the adapter has multiple docking stations and step of determining the orientation of the surgical tool from the database of stored values uses axis data for the location of each docking station.

* * * * *